(12) United States Patent
Okrut et al.

(10) Patent No.: US 9,575,042 B2
(45) Date of Patent: Feb. 21, 2017

(54) LIGAND-MODIFIED METAL CLUSTERS FOR GAS SEPARATION AND PURIFICATION

(71) Applicants: Alexander Okrut, Berkeley, CA (US); Xiaoying Ouyang, El Cerrito, CA (US); Ron Runnebaum, Berkeley, CA (US); Bruce C. Gates, El Macero, CA (US); Alexander Katz, Richmond, CA (US)

(72) Inventors: Alexander Okrut, Berkeley, CA (US); Xiaoying Ouyang, El Cerrito, CA (US); Ron Runnebaum, Berkeley, CA (US); Bruce C. Gates, El Macero, CA (US); Alexander Katz, Richmond, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/292,252

(22) Filed: May 30, 2014

(65) Prior Publication Data

US 2014/0356973 A1    Dec. 4, 2014

Related U.S. Application Data

(60) Provisional application No. 61/830,004, filed on May 31, 2013.

(51) Int. Cl.
| | |
|---|---|
| *G01N 33/00* | (2006.01) |
| *B01J 31/22* | (2006.01) |
| *B01J 20/22* | (2006.01) |
| *B01J 20/34* | (2006.01) |
| *C07C 7/12* | (2006.01) |

(Continued)

(52) U.S. Cl.
CPC ............ *G01N 33/004* (2013.01); *B01D 53/00* (2013.01); *B01D 53/02* (2013.01); *B01J 20/223* (2013.01); *B01J 20/3483* (2013.01); *B01J 31/2295* (2013.01); *C07C 7/12* (2013.01);

(Continued)

(58) Field of Classification Search
CPC ............. G01N 33/004; G01N 33/0036; G01N 33/0026; G01N 33/0006; G01N 33/00; Y10T 436/00; Y10T 436/20; Y10T 436/205831; B01J 31/2295; B01J 31/2282; B01J 31/22; B01J 31/16; B01J 20/223; B01J 20/22; B01J 20/00; B01J 20/3483; B01J 20/34

(Continued)

(56) References Cited

U.S. PATENT DOCUMENTS

| | | |
|---|---|---|
| 6,547,859 B1 | 4/2003 | Mullhaupt |
| 2012/0316347 A1 | 12/2012 | Katz et al. |
| 2013/0018199 A1 | 1/2013 | Katz et al. |

FOREIGN PATENT DOCUMENTS

KR    1020080064077    7/2008

OTHER PUBLICATIONS

Davies J. et al, Synthetic Coordination Chemistry: Principles and Practice, 1996, p. 260. obtained on Jun. 9, 2015.*

(Continued)

*Primary Examiner* — Christine T Mui
(74) *Attorney, Agent, or Firm* — E. Joseph Gess; Melissa M. Hayworth

(57) ABSTRACT

Provided is an organic ligand-bound metal surface that selects one gaseous species over another. The species can be closely sized molecular species having less than 1 Angstrom difference in kinetic diameter. In one embodiment, the species comprise carbon monoxide and ethylene. Such organic ligand-bound metal surfaces can be successfully (Continued)

used in gas phase separations or purifications, sensing, and in catalysis.

34 Claims, 9 Drawing Sheets

(51) Int. Cl.
  *B01D 53/00* (2006.01)
  *B01D 53/02* (2006.01)
(52) U.S. Cl.
  CPC .... *B01D 2253/20* (2013.01); *B01D 2257/502* (2013.01); *Y02P 20/52* (2015.11); *Y10T 436/205831* (2015.01)
(58) Field of Classification Search
  USPC .......................................... 436/134, 133, 127
  See application file for complete search history.

(56) References Cited

OTHER PUBLICATIONS

Okrut, Alexander et al. "Stabilization of coordinatively unsaturated Ir4 clusters with bulky ligands: a comparative study of chemical and mechanical effects" Dalton Translations v. 41:2091-2099 (2012).
Fielick, Andre et al., "The adsorption of CO on transition metal clusters: A case study of cluster surface chemistry, Surface Science", v. 60: 1427-1433.
International Search Report from corresponding International Application No. PCT/US2014/040260 mailed Oct. 22, 2014.
O. Khersonsky, D. S. Tawfik, Annu. Rev. Biochem. 79, 471-505 (2010).
P. G. Schultz, R. A. Lerner, Science 269, 1835-42 (1995).
P. J. O'Brien, D. Herschlag, Biochemistry 40, 5691-9 (2001).
L. Quintanar et al., J. Am. Chem. Soc. 127, 13832--45 (2005).
Y. Román-Leshkov, M. Moliner, M. E. Davis, Chem. Mater. 22, 2646-2652 (2010).
C. W. Jones, M. Tsapatsis, T. Okubo, M. E. Davis, Micropor. Mesopor. Mat. 42, 21-35 (2001).
C. B. Khouw, M. E. Davis, ACS Sym. Ser. 517, 206-221 (1993).
Goel et al. J. Am. Chem. Soc. 2012, 134, 17688-17695.
T. Degnan, J. Catal. 216, 32-46 (2003).
T. F. Degnan, C. M. Smith, C. R. Venkat, Appl. Catal. A-Gen. 221, 283-294 (2001).
A. Corma et al., Micropor. Mesopor. Mat. 38, 301-309 (2000).
C. P. Canlas et al., Nature Chem., 4, 1030-1036 (2012).
G. Wulff, B. Heide, G. Helfmeier, React. Polym. 6, 299-310 (1987).
Angew. Chem., Int. Ed. Engl. 34: 713 (1995).
Bauer et al., JACS 107, 6053 (1985).
C. David Gutsche, "Calixarenes" Part of the Monographs in Supramolecular Chemistry (J. Fraser Stoddard, ed.,: Royal Society of Chemistry, 1989).
C. David Gutsche, "Calixarenes Revisited" Part of the Monographs in Supramolecular Chemistry (J. Fraser Stoddard, ed.,: Royal Society of Chemistry, 1998).

\* cited by examiner

LIGAND-MODIFIED METAL CLUSTERS FOR GAS SEPARATION AND PURIFICATION

RELATED APPLICATION

This application claims priority to U.S. Provisional Patent Application Ser. No. 61/830,004 filed 31 May 2013, the contents of which are hereby incorporated by reference in their entirety.

This invention was made with government support under contract number DE-SC0005822 awarded by The Department of Energy. The government has certain rights in the invention.

BACKGROUND OF THE INVENTION

Field of the Invention

Unprecedented control of metal surface accessibility is facilitated by synthetic pockets associated with ligands bound to a metal. More particularly, a metal cluster core, e.g., an Ir core, with ligands, e.g., three calixarene phosphine ligands, bound thereto, can have binding sites accessible to one species, e.g., CO, but not another, ethylene. Such metal clusters can find application in catalysis and gas-phase separations.

Description of the Related Art

Enzymes have evolved to incorporate active sites within pockets that exhibit exquisite levels of specificity to reacting substrate molecules. (O. Khersonsky, D. S. Tawfik, *Annu. Rev. Biochem.* 79, 471-505 (2010)). Preferential substrate access and binding to active sites lead to significantly higher catalytic proficiencies for native substrate molecules, an observation that guided early understanding of accessibility in enzymes based on the well-known lock-and-key analogy, as well as the design of catalytic antibodies. (P. G. Schultz, R. A. Lerner, *Science* 269, 1835-42 (1995)) Preferential accessibility in these biological systems is thought to be controlled by the molecular-level structure and composition of the pocket enveloping the active site. (P. J. O'Brien, D. Herschlag, *Biochemistry* 40, 5691-9 (2001); L. Quintanar et al., *J. Am. Chem. Soc.* 127, 13832-45 (2005)). However, the features that control preferential accessibility are so subtle that, until now, attempts to create synthetic molecular pockets have fallen far short of replicating the degree of preferential binding and activation of reacting substrates found within biological systems.

In catalysis by synthetic materials, a high degree of shape selectivity is known to occur within the confines of interior micropores of zeolite crystals, (Y. Roman-Leshkov, M. Moliner, M. E. Davis, *Chem. Mater.* 22, 2646-2652 (2010); C. W. Jones, M. Tsapatsis, T. Okubo, M. E. Davis, *Micropor. Mesopor. Mat.* 42, 21-35 (2001); C. B. Khouw, M. E. Davis, *ACS Sym. Ser.* 517, 206-221 (1993)) but this often carries undesirable consequences of mass-transport limitations and limits the size of reactants and products to those that are small enough to access the interior active sites. Metal clusters encapsulated within a bulk microporous zeolitic framework are known to exhibit shape-selective binding due to the size discrimination characteristics of the zeolite (see Goel et al. *J. Am. Chem. Soc.* 2012, 134, 17688-17695). This is significantly different from the current invention in which selection of a fluid species arises due to the spatial arrangement and local environment created by ligands directly bound to the metal surface, rather than the microporosity of an encapsulating bulk framework. Another type of less well-developed shape selectivity in synthetic active sites, the nest effect, (T. Degnan, *J. Catal.* 216, 32-46 (2003)), relates to shape selectivity of an active site that is located at the terminus of a micropore on the external surface. In contrast to shape selectivity imposed within the interior of a zeolite catalyst, the nest effect is the closest analogy to shape-selective catalysis in enzymes, because of shape-selectivity being induced via active-site location within a surface pocket rather than a three-dimensional cavity of a bulk material. A nest effect has been used to explain shape selectivity on the external surfaces of zeolites, (T. F. Degnan, C. M. Smith, C. R. Venkat, *Appl. Catal. A-Gen.* 221, 283-294 (2001); A. Corma et al., *Micropor. Mesopor. Mat.* 38, 301-309 (2000)) and in surface-imprinting strategies. (C. P. Canlas et al., *Nature Chem.*, 4, 1030-1036 (2012), G. Wulff, B. Heide, G. Helfineier, *React. Polym.* 6, 299-310 (1987)). However, to-date, selectivities achieved when using the nest effect have been modest, even for molecules of significantly differing size, and do not approach the selectivity that would be useful to industry for applications such as separations involving a multicomponent fluid mixture and sensing. Such a separation typically involves adsorbing one or more components from a fluid mixture preferentially over others within the same mixture. The fluid may be either gas phase or liquid phase. A sensing application would involve the preferential adsorption of one or more components from a fluid mixture, which would be used to determine the presence and/or relative amounts of these component(s) in the mixture.

SUMMARY OF THE INVENTION

Provided is an organic ligand-bound metal surface that selects one fluid, e.g., gaseous, species over another. The species can be closely sized molecule species having less than 1 Angstrom difference in kinetic diameter. In one embodiment, the species comprise carbon monoxide and ethylene. In another embodiment, the ligand bound metal is a metal cluster having one or more vacant binding sites. In this context, vacant binding sites are binding sites that could be occupied by a ligand because there is a coordination site available to bind a suitable ligand, but instead remains unoccupied. The binding sites are selective with regard to binding one fluid species over others. The remarkable aspect of this selective binding is that it does not rely on a competitive binding situation. That is to say, one or more species are substantially excluded from binding, even when said species bind strongly to the metal intrinsically (i.e. when the metal surface is accessible to said species). When treating binding sites with said species, open binding sites are remarkably preserved, in the absence of other species that are able to access and bind. This is significantly different from a situation in which competitive binding is required in order to achieve separation of one component from another, wherein open binding sites are saturated with a component in a mixture that binds preferentially relative to other component(s). In the latter competitive binding situation, it is impossible to retain open binding sites and have selective exclusion of one or more components in a mixture, which intrinsically bind strongly to the metal.

Among other factors, by the present invention unprecedented control of metal surface accessibility has been achieved. For example, in a supported $In_4$ cluster catalyst controlled accessibility is facilitated by synthetic pockets associated with three calixarene phosphine ligands bound to the cluster. Vacant binding sites are created on the cluster by removal of initially present CO ligands by simple dissociation in flowing gas or, alternatively, by a new method consisting of reactive decarbonylation with the bulky reactant trimethylamine-N-oxide (TMAO). Both lead to metal sites that are accessible to CO. Reactive decarbonylation also creates sites that are accessible to ethylene—and these catalyze its hydrogenation. The concept of synthesizing vacancies on the surface of a metal and simultaneously creating pockets for selective access to them can have wide-ranging applications in areas such as catalysis and gas-phase separations. The selectivity observed between binding CO and completely sieving out ethylene, for example, has not heretofore been achieved.

DETAILED DESCRIPTION OF THE INVENTION

Figure 1:
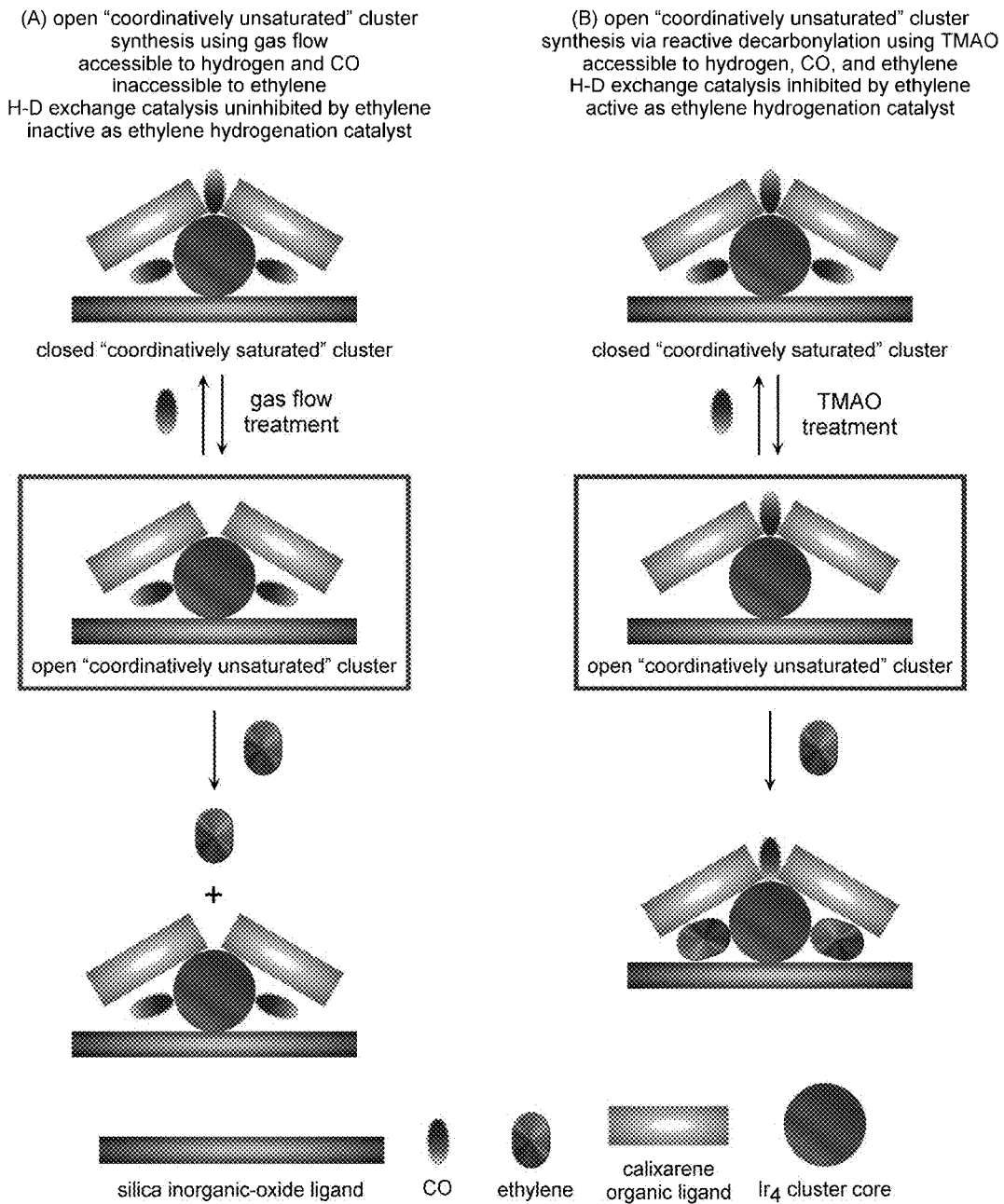
FIG. 1 shows a schematic representation of various sites on a supported molecular cluster catalyst. Open sites in (A) are highly selective in their ability to bind hydrogen and CO but not ethylene, whereas open sites in (B) bind hydrogen, CO, and ethylene.

The present invention provides an organic ligand-bound metal surface that selects one gaseous species over another. In this context, metal surface refers to a surface that is created by two or more metal atoms connected with metal-metal bonds. By "selects" is meant that the ligand-bound metal surface is inaccessible to one species, but accessible to the other. By inaccessible is meant that the species is substantially excluded by the ligand-bound metal surface, even when treating with this species in the absence of others that bind, with the other species binding relatively easily. This has been found possible even when the selection of species is between two closely sized molecular species having less than 1 Angstrom difference in kinetic diameter. The two species carbon monoxide and ethylene are an example. The carbon monoxide has been found to bind to the metal surface quickly, whereas the ethylene does not bind and finds the ligand-bound metal surface inaccessible, even though intrinsically, ethylene binds strongly to iridium metal (i.e., when the metal surface is accessible to ethylene). Carbon monoxide could be in a mixture of gases, for example, including ethylene, hydrogen sulfide or mercaptan, water, carbon dioxide, nitrogen and even hydrogen, and it has been found that the carbon monoxide would be selectively bound to the ligand-bound metal surface.

The metal can be any suitable metal core, for example, a metal cluster or a metal nanoparticle. Metals such as Ir, Rh, Pt, Re, Ru, Au, Pd, Ni, Mo, W, Os and Co can be used, though this list is not exhaustive and does not limit the practice of the invention in any way. Among the metal clusters, Ir$_4$, Rh$_4$, and metal clusters consisting of a tetrahedral framework are preferred. These examples of metal clusters are not limiting; metal cores of various sizes can be applied; there is no restriction to the uniformity of the metal clusters. In addition, combinations of metals can also be used (e.g., bimetallic clusters, trimetallic clusters, and so forth). The term comprised of either metal cluster or metal nanoparticle as used herein also refers to colloids comprised of bridging ligands within either the cluster (such as iron-sulfur clusters used in proteins and enzymes in biological systems) or nanoparticle (such as metal oxide nanoparticles, CdS, or CdSe).

The ligands can be any suitable ligand, generally an electron donating ligand bound to the metal. In one embodiment, calixarene ligands are used and have been found to be especially useful. Their size facilitates stable open binding sites on the metal cluster surface as described previously; for example, see U.S. 20120316347 A1, which is incorporated herein by reference in its entirety. In a preferred embodiment, the ligand can be any ligand (including ligands that do not consist of a calixarene) that has a radius of curvature that is substantially larger than that of the metal cluster core to which the ligand is bound.

Calixarenes are a well-known class of cyclic oligomers that are usually made by condensing formaldehyde with p-alkylphenols under alkaline conditions. V. Bohmer summarized the chemistry of calixarenes in an excellent review article (*Angew. Chem., Int. Ed. Engl.* 34: 713 (1995). Early transition metal complexes in which the four oxygen atoms of calix[4]arenes or O-methylated calix[4]arenes chelate to the metal are now known (see, e.g., *J. Am. Chem. Soc.* 119: 9198 (1997)).

Calixarene-related compounds can also be used and include, for example, oxacalixarenes, azacalixarenes, silicacalixarenes and thiacalixarenes, which contain one or more oxygen, nitrogen, silicon or sulfur bridges, respectively, between phenolic groups, as well as calixarene compounds having one or more platinum bridges. This term also includes compounds such as those termed "calixarene-related cyclooligomers" in Gutsche (1998), for instance similar structures formed from furan or thiophene rather than phenolic residues. Other calixarene-related compounds include, for example, calix[n]pyrroles, calix[m]pyridino[n]pyrroles or calix[m]pyridine. A "calix[n]pyrrole," is a macrocycle having "n" pyrrole rings linked in the .alpha.-positions. "Calix[m]pyridino[n]pyrroles" are macrocycles having "m" pyridine rings and "n" pyrrole rings linked in the .alpha.-positions. A "calix[m]pyridine" is a macrocycle having "m" pyridine rings linked in the .alpha.-positions. In addition, within the context of this invention, other macrocycles such as suitably substituted cyclodextrins can also be considered calixarene-related compounds, as calixarenes are known as the synthetic equivalents of cyclodextrins.

The framework of the calixarene ligand can be substituted with other atoms that do not interfere with the ability of the ligand to form complexes with metals. For example, the framework of the calixarene ligand can be substituted with alkyl, aryl, halide, alkoxy, thioether, alkylsilyl, or other groups.

Exemplary calixarene-related compounds have four, six, or eight phenolic moieties; thus preferred calixarenes are calix[4]arenes, calix[6]arenes, and calix[8]arenes. Calix[4] arenes are more preferred. In some preferred catalyst systems, the calixarene ligand is a p-alkylcalixarene, more preferably a p-t-butylcalixarene. The synthetic procedures for making these materials have been finely honed and optimized, and the starting materials, e.g., p-t-butylphenol, are readily available.

Exemplary calixarene-related compounds are calixarenes, which are cyclic oligomers of phenol and substituted phenols condensed with formaldehyde, and are characterized by the general structure:

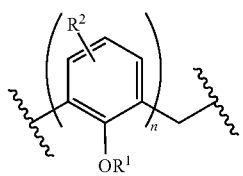

in which n is 3, 4, 5, 6, 7, 8, 9, 10, 11, 12, 13, 14, 15 or 16 in various embodiments. In exemplary embodiments, n is 4. The wavy lines represent the attachment of a plurality of these monomeric units to form a closed ring. General information about such molecules can be found, for example in Bauer et al., JACS 107, 6053 (1985) and the texts "Calixarenes" by C. David Gutsche, which is part of the Monographs in Supramolecular Chemistry (J. Fraser Stoddart, ed.; Royal Society of Chemistry, 1989) and "Calixarenes Revisited" (1998) by the same author. Calixarenes are in the form of a cyclical oligomer having a "basket" shape, where the cavity can serve as a binding site for numerous guest species, including ions and molecules.

In some embodiments, the group $R^2$ may be hydrogen, or may be any of a number of aryl substituent groups including, but not limited to, alkyl, alkenyl, alkynyl, allyl, aryl, heteroaryl, alcohol, sulfonic acid, phosphine, phosphine oxide, phosphonate, phosphonic acid, thiol, ketone, aldehyde, ester, ether, amine, quaternary ammonium, imine, amide, imide, imido, nitro, carboxylic acid, disulfide, carbonate, isocyanate, carbodiimide, carboalkoxy, carbene, sulfoxide, phosphonium, carbamate, acetal, ketal, boronate, cyanohydrin, hydrazone, oxime, oxazole, oxazoline, oxalane, hydrazide, enamine, sulfone, sulfide, sulfenyl and halogen. In exemplary calixarenes, $R^2$ typically represents a single substituent at the position para to the $OR^1$ group. However, calixarenes of use in the present invention can include one or more $R^2$ substituent. When more than one substituent is present, the substituents can be the same or different. An exemplary class of calixarene compounds with two substituents is known in the art as the calix[n]resorcinarenes, which comprise resorcinol moieties that are joined to each other, and typically possess phenoxy groups in a different arrangement around the ring.

Exemplary $R^1$ substituents include substituted or unsubstituted alkyl, substituted or unsubstituted heteroalkyl, substituted or unsubstituted aryl and substituted or unsubstituted heteroaryl moieties. $R^1$ can also be H.

In exemplary embodiments, at least one $R^1$ comprises one or more coordinating atoms. A "coordinating atom" is a component that is capable of coordinating (or forming a coordinate bond) with a metal atom, especially a metal atom of a metal colloid. Exemplary "coordinating atoms" include nitrogen, oxygen, sulfur, phosphorus and carbon (for example, as in carbene). The coordinating atom can be neutral or charged, e.g., a component of a salt or derived therefrom.

The ligands, such as calixarene ligands, are generally functionalized with a group that bonds to the metal. This group is generally referred to as a linker group, which is part of the ligand.

The term "linker" as used herein refers to a single covalent bond ("zero-order") or a series of stable covalent bonds incorporating 1-30 nonhydrogen atoms selected from the group consisting of C, N, O, S, Si, B and P that covalently link together the components of the invention disclosed herein, e.g., linking a solid support to a calixarene-related compound, or linking a calixarene-related compound to a metal core. Exemplary linkers include 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 non-hydrogen atoms. Unless otherwise specified, "linking," "linked," "linkage," "conjugating," "conjugated" and analogous terms relating to attachment refer to techniques utilizing and species incorporating linkers. A calixarene-related compound can comprise multiple linkers, thus conferring higher levels of denticity.

In some embodiments, a linker is a moiety selected from phosphine, substituted or unsubstituted alkyl, substituted or unsubstituted heteroalkyl, substituted or unsubstituted aryl and substituted or unsubstituted heteroaryl.

In exemplary embodiments, a linker comprises a coordinating atom. In exemplary embodiments, the coordinating atom is selected from phosphorus, carbon, nitrogen and oxygen. Coordinating atoms can be provided through a large number of various moieties known in the art. For convenience, these moieties can be referred to as P-, C-, N- and O-containing moieties.

In exemplary embodiments, a linker is a P-containing moiety. One particularly useful P-containing moiety is phosphine. In various exemplary embodiments, the coordinating atom on the linker is the phosphorus atom of a phosphine moiety. In some embodiments, the term "phosphine" generically refers to —$Y^1P(Y^2)(Y^3)$, wherein $Y^1$ is selected from a bond, substituted or unsubstituted alkyl, substituted or unsubstituted heteroalkyl, substituted or unsubstituted aryl and substituted or unsubstituted heteroaryl; and $Y^2$ and $Y^3$ are independently selected from substituted or unsubstituted alkyl, substituted or unsubstituted heteroalkyl, substituted or unsubstituted aryl and substituted or unsubstituted heteroaryl. In some embodiments, $Y^2$ and $Y^3$ are each substituted or unsubstituted aryl. In exemplary embodiments, $Y^2$ and $Y^3$ are each phenyl. In some embodiments, $Y^1$ is substituted or unsubstituted alkyl. In some embodiments, $Y^1$ is $C_1$, $C_2$, $C_3$, $C_4$, $C_5$ or $C_6$ alkyl. In some embodiments, $Y^1$ is methyl. In some embodiments, $Y^1$ is a bond.

The ligand-bound metal cluster of the present invention can achieve its selectivity by having one or more vacant binding sites. It is these binding sites, generally between several ligands, which are selective with regard to binding one gaseous species over another. These binding sites can be synthesized on the surface of the metal by removal of an initially present ligand, e.g., CO. When the ligand removed is CO this is defined as the process of decarbonylation. Decarbonylation can occur with a fraction of a CO ligand (on average) per cluster. More preferably, decarbonylation can occur with at least one CO ligand per cluster. Most preferably, decarbonylation can occur with one or more CO ligands per cluster. The removal can be achieved by simple dissociation in flowing gas, or by a reaction. In the case of CO, reactive decarbonylation with a bulky reactant trimethylamine-N-oxide (TMAO) has been found successful.

The ligand-bound metal surfaces or metal clusters can be used as is or bound to a solid support. Silica is a preferred solid support. But, in general, the sold support can comprise any porous or nonporous oxide. Other suitable supports include alumina, silica-alumina or others; carbon or mesoporous carbon; crystalline aluminosilicate zeolite; a delaminated form of layered zeolite precursor; a zeolite nanosheet; and layered materials such as clays.

The ligand-bound metal surfaces or metal clusters, whether supported or not, can be used easily within the temperature range of room temperature and 300° C. Suitable temperatures can also be much higher or lower depending on the particular application. Applications include gas sensing, gas separation, gas purification, catalysis, etc.

Leveraging the catalytic proficiency of metal clusters, unprecedented control of accessibility, binding, and catalytic activation of reacting substrates in a synthetic pocket, using a supported molecular cluster has been demonstrated. The pocket is generally located at the interface of a metal cluster core and ligands bound to it, and controls substrate access to the surface of the core. FIG. 1 shows schematics of closed "coordinatively saturated" active sites, as well as two types of site environments corresponding to open ("coordinatively unsaturated") active sites: (a) open active sites that bind hydrogen and CO but not ethylene; and (b) open active sites that bind CO, hydrogen, and ethylene and catalyze the reaction of the latter two to make ethane. Each of the open active sites is created by removing a CO ligand from the metal cluster, but the two sites in FIGS. 1a and 1b have sharply different accessibility profiles and abilities to discriminate between $H_2$ (with a kinetic diameter of 2.31 Å) and CO (kinetic diameter of 3.28 Å), on the one hand, and ethylene (kinetic diameter 3.86 Å), on the other. The remarkable feature of the controlled accessibility of sites in FIG. 1a is that they absolutely discriminate between two molecules that differ in their kinetic diameters by less than 0.6 Å: ethylene (inaccessible) and CO (accessible), whereas sites in FIG. 1b are accessible to both molecules. Such a highly refined discrimination between two molecules has not been observed in synthetic pockets on surfaces. The types of sites shown in FIG. 1a have immediate and evident ramifications on processes such as separations of CO from olefins in gas mixtures via selective CO adsorption. They can also be used as selective catalysts by either excluding certain reactant species from accessing the metal surface, in a fashion similar to molecular sieves, or, alternatively, limiting the rates of formation of certain products on the metal surface due to steric considerations.

One of the simplest possible stable metal surfaces, consisting of a four-atom tetrahedral core in the $Ir_4$(phosphine)$_3$(CO)$_9$ cluster was used. Active sites were created on this surface that consist of open centers by controlled removal of CO ligands. The other ligands are phosphines and a mesoporous silica surface (the silica by itself offers no control of selectivity)—the silica is a support, which has been chosen for "site isolation" of the clusters, so that each one acts independently of the others. The phosphine ligands play a dual role in (i) donating electron density to make the metal core highly electron rich, which greatly affects binding and ligand exchange processes on the metal surface, and (ii) acting as a steric barrier against aggregation/coalescence of the clusters while simultaneously facilitating access to open sites on the underlying metal surface.

Figure 2:
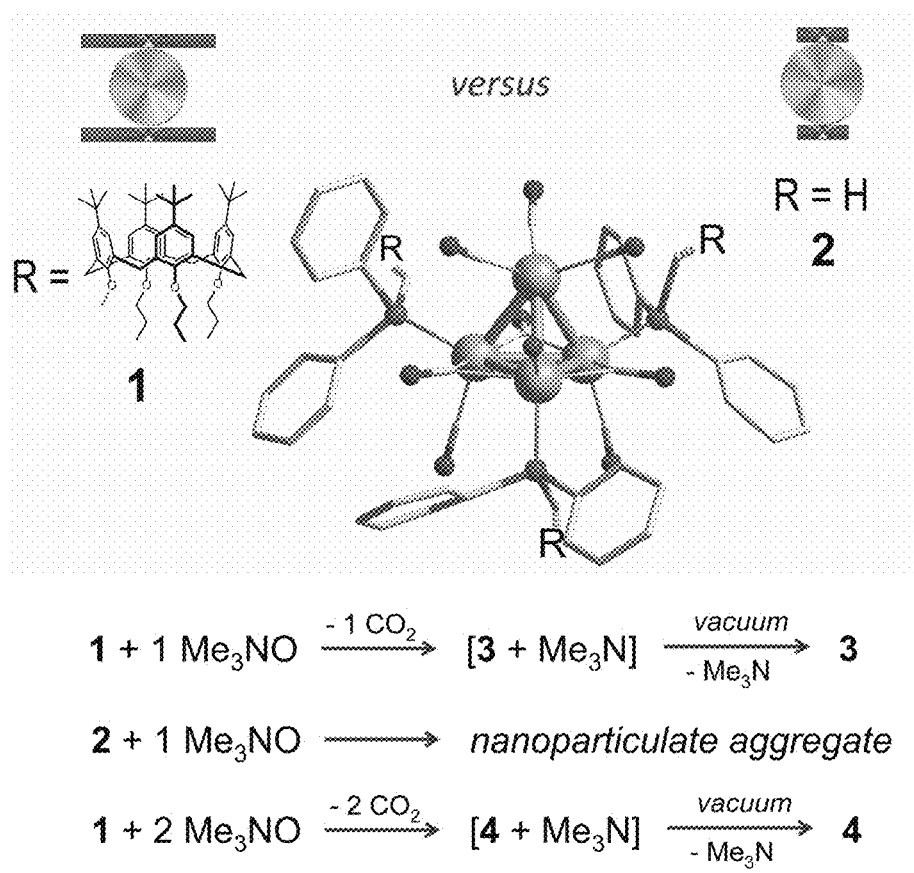
FIG. 2 shows a schematic representation of $Ir_4(CO)_9$(phosphine)$_3$ clusters consisting of a calixarene phosphine in 1 and PPh$_2$Me in 2. The bottom panel represents the method of synthesizing a vacancy by reactive decarbonylation using TMAO. This procedure is used to synthesize stable calixarene-bound open clusters 3 and 4.

It is believed that the a role of the bulky phosphine ligands in stabilizing a supported cluster consisting of open sites is akin to the role of bumpers on bumper cars, whereby large calixarene substituents on the phosphines prevent cluster core aggregation and coalescence while allowing access to the underlying metal surface. Such a mechanical model of ligand stabilization of open sites relies on neighboring metal centers—as are available on a cluster—and is difficult to achieve in conventional metal complexes that lack such neighboring metal sites. The roles of the phosphine ligands in stabilizing $Ir_4$ clusters with open sites were used by comparing bulky calixarene and smaller non-calixarene phosphine ligands. These are represented schematically by clusters 1 (calixarene) and 2 (non-calixarene) in FIG. 2.

The resulting stable, open clusters were used for catalytic H-D exchange (in the reaction of $H_2+D_2$) and for catalytic ethylene hydrogenation, as these are among the catalytic probes of such open sites that are most sensitive to the sizes of the reacting molecules. These reactions form a basis for understanding hydrogen dissociation and hydrogen transfer generally, illustrated by energy-related examples such as hydrodesulfurization of compounds in petroleum, which is essential for production of clean-burning low-sulfur fuels, and selective ring opening of polynuclear aromatic hydrocarbons, which is crucial for their upgrading to hydrogen-rich, environmentally benign fuels. Elucidating the subtle interplay between substrate accessibility and catalysis in these reactions from a control-of-structure perspective is therefore valuable to rational catalyst design. The comparison in FIGS. 1a and 1b shows how the various types of open sites perform in catalysis, illustrating control of ethylene access to an open site on the metal surface and the interplay between this access and catalysis on the site for these prototypical catalytic reactions. The latter is currently unknown for catalytic ethylene hydrogenation, and provides unique insight into the relationships between supported metal cluster catalyst structure and function in general.

EXPERIMENTAL

The following materials were prepared and used in the following experiments:

Preparation of $SiO_2$-500

Aerosil 200 was kindly provided by Evonik Industries AG. Ten grams of Aerosil 200 were mixed with 200 mL nanopure water. The mixture was heated at 120° C. under vigorous stirring for 24 h. After the mixture was cooled to room temperature, the slurry was centrifuged and the water phase was decanted. The solid was dried at 200° C. for 15 h under vacuum. After cooling to room temperature, the solid material was thoroughly crushed with mortar and pestle. The obtained powder was then treated in a flow bed reactor as followed: flow of dry air (110 mL/min) and argon (55 mL/min), temperature program: 5° C./min ramp to 95° C., soak for 20 min, 5° C./min ramp to 500° C., soak 4 h, turn off dry air flow, lower argon flow to 15 ml/min, hold 500° C. for 10 h, cool to room temperature. The powder was then stored in vials in a glove box under argon atmosphere.

Preparation of 1-$SiO_2$-500

A solution of 51 mg (0.013 mmol) cluster 1 in 3 mL freshly distilled hexane was added to slurry of 949 mg $SiO_2$-500 and 20 mL hexane. The mixture was stirred for 1 h and the hexane was evaporated. The remaining powder was dried under vacuum at room temperature for 0.5 h.

Preparation of 3-$SiO_2$-500 and 4-$SiO_2$-500

Synthesis of 3-$SiO_2$-500: To a solution of 51 mg (0.013 mmol) cluster 1 was added 100 μL, of a solution of 100 mg (1.33 mmol) $Me_3NO$ in 10 mL dichloromethane. The solution color changed immediately from yellow to brown. The solution was stirred for 1 h and added to slurry of 949 mg $SiO_2$-500 and 20 mL hexane. The mixture was stirred for 1 h and the hexane was evaporated. The remaining powder was dried under vacuum at room temperature for 0.5 h.

Synthesis of 4-$SiO_2$-500: To a solution of 51 mg (0.013 mmol) cluster 1 was added 195 μL of a solution of 100 mg (1.33 mmol) $Me_3NO$ in 10 mL dichloromethane. The solution color changed immediately from yellow to brown. The solution was stirred for 1 h and added to slurry of 949 mg $SiO_2$-500 and 20 mL hexane. The mixture was stirred for 1 h and the hexane was evaporated. The remaining powder was dried under vacuum at room temperature for 0.5 h.

Results

Figure 3:
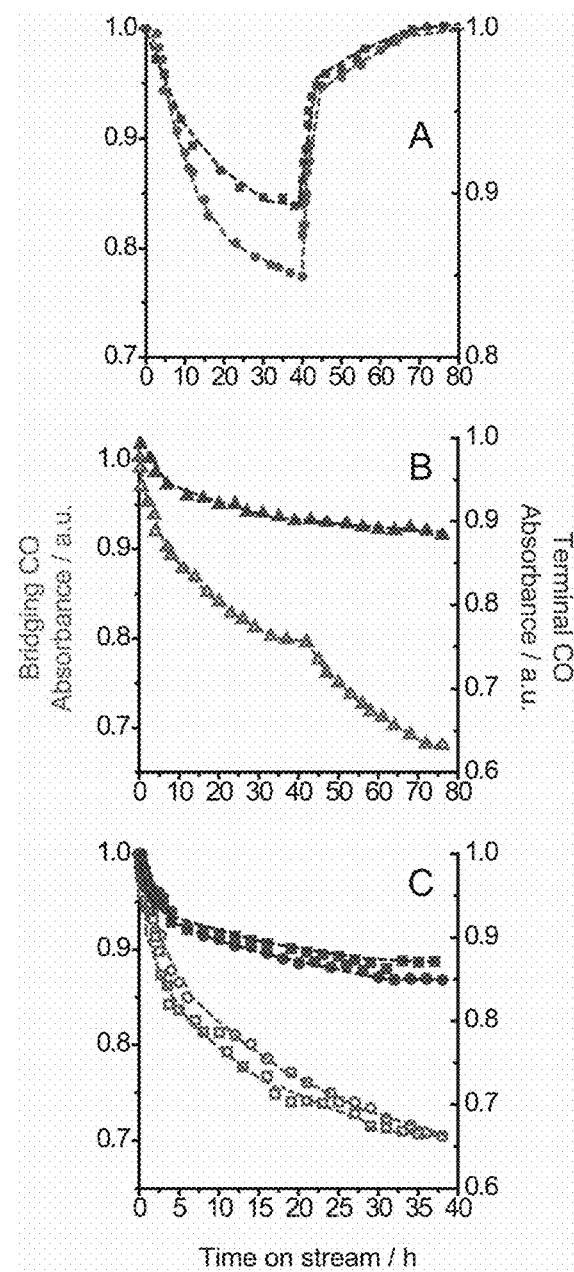
FIG. 3 shows an IR spectra corresponding to bridged and terminal CO integrated intensity versus time. (A) squares (terminal CO) and circles (bridging CO) represent sample 1-SiO$_2$-500 during the following treatment: 40 h in flowing helium followed by 40 h in flowing CO. (B) Filled (terminal CO) and open (bridging CO) triangles represent sample 1-SiO$_2$-500 during the following treatment: 40 h in flowing helium followed by 40 h in flowing ethylene. (C) Filled (terminal CO) and open (bridging CO) circles represent sample 1-SiO$_2$-500 during the following treatment: 40 h in flowing ethylene. Filled (terminal CO) and open (bridging CO) squares represent sample 3-SiO$_2$-500 during the following treatment: 40 h in flowing ethylene. Helium and CO (2% in helium) flowed at a rate of 50 mL/min (NTP), ethylene flowed at a rate of 20 mL/min (NTP), and the temperature was maintained at 40° C. for all treatments. The sample masses were 15 to 20 mg. The integrated intensity is normalized to its value immediately prior to gas treatment (time on stream=0).

Open active sites for binding and catalysis were synthesized by cluster decarbonylation, using either (i) flowing inert gas for simple CO dissociation or (ii) reactive decarbonylation via treatment with TMAO (trimethylamine oxide), which was found to actually synthesize open sites by selectively oxidizing bound CO and releasing $CO_2$ to the gas phase. Control of accessibility to open sites formed by using methods (i) and (ii) above were compared. Treatment of the closed (coordinatively saturated) cluster 1 supported on silica-500 (silica-500 denotes partially dehydroxylated silica that has been pretreated at 500° C.)—denoted as 1-$SiO_2$-500—with flowing helium at 40° C. for 40 h led to measurable decarbonylation, as shown in FIG. 3a. Recarbonylation of these open sites occurred rapidly upon exposure to CO gas, as shown in FIG. 3a, to regenerate the supported closed cluster 1-$SiO_2$-500. Thus, this synthesis of clusters with open sites was readily and fully reversible. When the supported clusters with open sites derived from this approach (i.e., after 40 h of helium flow) were subsequently treated with flowing ethylene for 40 h at 40° C., there was additional decarbonylation, as shown in FIG. 3b. However, there was no ethylene binding after this latter ethylene treatment, as shown by the absence of ethylene-related bands observed in the subtraction infrared (IR) spectrum of FIG. 4a, despite the known strong affinity of ethylene for iridium sites. The same result of lack of ethylene binding via IR subtraction spectrum was observed when treating the same cluster as above (1-$SiO_2$-500) with He for a longer 250 h duration followed by 40 h of ethylene gas flow, under otherwise similar conditions as above. An additional experiment aimed at synthesizing vacancies on the supported cluster via treatment in flowing gas consisted of treating 1-$SiO_2$-500 with ethylene alone for 40 h at 40° C. Data in FIG. 3c show that this treatment also led to a degree of decarbonylation similar to that observed during the treatments in flowing helium (FIGS. 3a and 3b). However, this treatment also led to no ethylene binding, as shown by the difference spectrum in FIG. 4b. Thus, in all cases, treatment of closed supported molecular cluster 1-$SiO_2$-500 in flowing gas results in open sites on the metal that are prevented from binding ethylene by the bulky ligands. The accessibility of the open sites resulting from treatment in flowing gas is sharply dependent on the size of the intruding molecule—ethylene being completely sieved out but CO not. This observation requires that CO vacancies derived from treatment in flowing gas be located within sterically confined pockets, which are located at the interface between the metal cluster core and the ligands bound to this core and which do not permit the entry and binding of ethylene even after a lengthy (40 h) exposure.

Given the small (<0.6 Å) size difference between these two molecules, the demonstration that sterics determine that CO but not ethylene is accessible to an active site is an unprecedented example of molecular recognition by a synthetic pocket on a surface. This is an example that harnesses the power of self assembly within a ligand monolayer to achieve this discrimination. Previously, self assembly has been used to synthesize structures that discriminate between similarly sized molecules, but this has been achieved only within the context of a three-dimensional crystal-growth assembly—not a monolayer pocket as reported here.

To further control the accessibility to the metal surface, a new method was used to synthesize CO vacancies—not just simple dissociation of this ligand as described above—but instead a reaction with the bulky oxidant TMAO. This choice was based on the premise that such a bulky oxidant would remove a different set of CO ligands from those that were simply dissociated under gas flow conditions, based on its limited access due to the steric bulkiness of TMAO and the interference of ligands bound to the cluster. It was believed that this reactive decarbonylation could lead to synthesis of CO vacancies within larger pockets than those formed by simple CO dissociation, akin to FIG. 1b rather than FIG. 1a. This does not limit the invention. The open clusters 3 and 4 were thus synthesized via TMAO treatment of the closed cluster 1 in alkane solvent. Like treatment in flowing gas, treatment with TMAO also led to removal of both terminal and bridging CO ligands, which was followed by observing the decreasing integrated carbonyl stretching band intensity by IR spectroscopy (Table 1) below. These data show that decarbonylation is unselective to any particular CO ligand when TMAO is used, although most of the decarbonylation results in the removal of bridging rather than terminal CO ligands. The number of CO ligands removed matches the number of TMAO molecules used in the synthesis of these clusters from 1. The reversibility of decarbonylation upon TMAO treatment of clusters 3 and 4 in solution was assessed by treating the decarbonylated clusters in decane with CO at 1.2 bar. Such treatment resulted in significant amounts of CO rebinding to 3 and 4, as summarized in Table 1, and the results demonstrate the reversibility of cluster 1 decarbonylation when TMAO is used.

unique protective role of the calixarene ligand. The ability of this bulky ligand to act as such a protective barrier while still facilitating access to the open cluster sites reinforces our previous results and the mechanism shown schematically in FIG. 2. This role of the calixarene can be elucidated by the high radius of curvature of this ligand relative to that of the metal cluster core.

Figure 4:
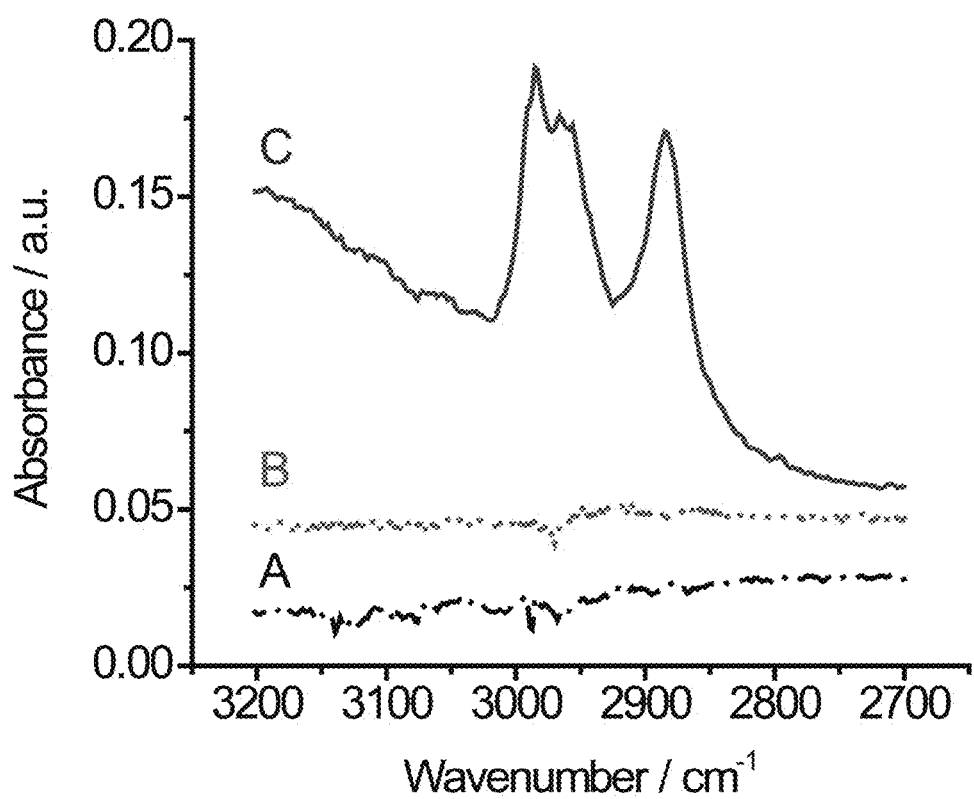
FIG. 4 shows an FTIR subtraction spectra consisting of (A) 1-SiO$_2$-500 before and after 40 h of treatment in flowing helium followed by 40 h of treatment in flowing ethylene at room temperature; (B) 1-SiO$_2$-500 before and after 40 h of treatment in flowing ethylene at room temperature; (C) 3-SiO$_2$-500 before and after 40 h of treatment in flowing ethylene at room temperature.

A key result is that the data demonstrate a sharp contrast between the pockets in the clusters decarbonylated by simple CO dissociation and those in the clusters decarbonylated by reaction with TMAO. Ethylene bonds to the latter (the open cluster $3-SiO_2-500$, following reactive decarbonylation, FIG. 4c), whereas it does not bond at all to either the closed cluster $1-SiO_2-500$ or the cluster synthesized by removal of CO via simple dissociation, by treatment in flowing helium/ethylene or ethylene alone, as shown in FIGS. 4a and 4b. The data therefore demonstrate two types of open sites formed from the $Ir_4$ carbonyl clusters. One type of site results from treatment in flowing gas that removes some CO but generates only sites that are unable to bind ethylene, although they readmit CO, akin to sites in FIG. 1a. It is evident that the types of sites described in FIG. 1a can be useful for the separation of CO via its adsorption from gas-phase mixtures involving olefin and CO, which is an industrially relevant separation. Another type of site results from reactive decarbonylation by TMAO, and these sites

TABLE 1

Characterization of cluster samples 1-4 using integrated IR carbonyl-band absorbance intensities[a] after reactive decarbonylation using TMAO, and subsequent recarbonylation, in decane solution.

| | | Decarbonylation | | | Recarbonylation | | |
|---|---|---|---|---|---|---|---|
| Sample | | I(CO) | I(CO) | #(CO)[c] | I(CO) | I(CO) | #(CO) |
| Cluster | TMAO[b] | terminal/% | bridging/% | removed | terminal/% | bridging/% | gained |
| 1 | 0 | 100 | 100 | 0 | n.A. | n.A. | n.A. |
| 2 | 0 | 100 | 100 | 0 | n.A. | n.A. | n.A. |
| 3 | 1 | 92 | 73 | 1.3 | 98 | 85 | 0.7 |
| 4 | 2 | 87 | 54 | 2.1 | 93 | 72 | 0.9 |
| 2 after TMAO | 1 | 24 | 2 | 7.5 | 38 | 23 | 1.5 |

Figure 8:
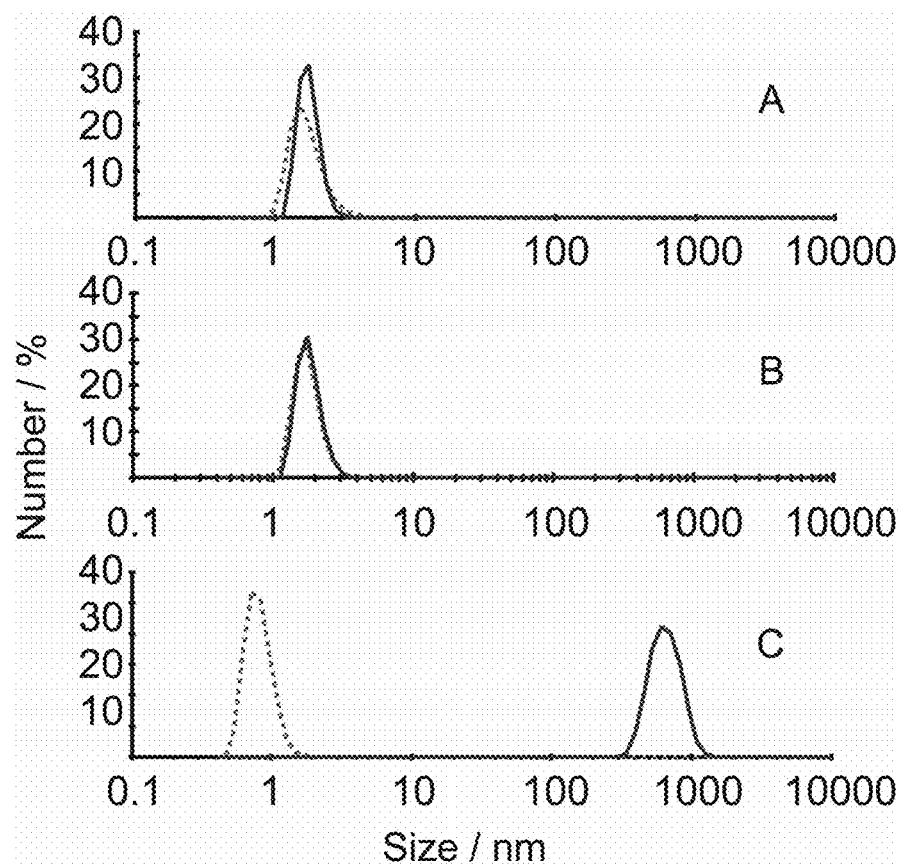
FIG. 8 shows a size distribution according to dynamic light scattering for 4.3 µM decane solutions of (A) 1 (dashed line), 3 (solid line); (B) 1 (dashed line), 4 (solid line); (C) 2 (dashed line), 2 following TMAO treatment (solid line).

[a]Absorbance intensities were integrated from 1927 $cm^{-1}$ to 2084 $cm^{-1}$ for terminal CO ligands and from 1718 $cm^{-1}$ to 1875 $cm^{-1}$ for bridging CO ligands in all samples; n.A. refers to "not applicable" since no recarbonylation is possible on clusters that lack open binding sites.
[b]Amount of TMAO per $Ir_4$ cluster used for synthesis of open "coordinatively unsaturated" clusters in decane solution
[c]# = number of CO molecules removed via reactive decaronylation per $Ir_4$ cluster using TMAO in decane solution DLS (dynamic light scattering) data show that the size of the open iridium cluster frameworks in 3 and 4 is unchanged relative to that of closed cluster 1. In sharp contrast, DLS data demonstrate cluster aggregation via formation of macroscopic particles >500 nm in diameter, upon similar treatment of the clusters 2 incorporating the smaller $PPh_2Me$ ligand with a single equivalent of TMAO. This evidence of cluster aggregation during decarbonylation of 2 is bolstered by IR data, which show a pronounced frequency shift in the CO IR bands upon treatment of 2 with a single equivalent of TMAO, as well as a disproportionately large intensity decrease (Table 1 above). In contrast, the lack of observed frequency changes for all CO bands for 3 and 4 relative to 1 strongly supports the inference of stability of these open clusters, as further supported by DLS data shown in FIG. 8 and STEM microscopy images of supported clusters.

The lack of observed cluster aggregation during decarbonylation of 1, which incorporates the sterically bulky calixarene-phosphine ligand, compared with the significant aggregation observed when the smaller $PPh_2Me$ ligand was present instead during decarbonylation of 2, underscores the bind both ethylene and CO, akin to sites in FIG. 1b. Details are provided in the following paragraph.

The ability of $3-SiO_2-500$ to bind ethylene by treatment in flowing ethylene at 40° C. for 40 h was observed. This treatment failed to lead to any ethylene binding to $1-SiO_2-500$ (closed) (FIGS. 3c and 4b). During this treatment, $3-SiO_2-500$ underwent similar degrees of decarbonylation relative to $1-SiO_2-500$, as shown in FIG. 3c. In contrast to results from treatment of $1-SiO_2-500$ (closed) in flowing gas, there are distinct bands assigned to ethylene in FIG. 4c, which represents the difference spectrum (spectrum after ethylene treatment—spectrum before ethylene treatment) for $3-SiO_2-500$ following this ethylene treatment. Those between 2884 and 2990 $cm^{-1}$ in FIG. 4c are assigned to di-σ-bound ethylene, ethyl, or ethylidyne ligands bonded to $Ir_4$ in $3-SiO_2-500$. Similar bands have been previously assigned for supported $Ir_4$ clusters during ethylene hydrogenation catalysis. The absence of π-bonded ethylene bands observed in FIG. 4c at wavenumbers above 2900 $cm^{-1}$ is consistent with the much weaker binding of π-bonded ethylene relative to the σ-bonded intermediates described above. However, the results do not preclude the presence of π-bonded ethylene on the cluster surface during ethylene treatment, as this species could have desorbed during the brief period of helium flow applied to purge unbound gas-phase ethylene from the system prior to spectroscopic analysis. The formation of ethylidyne ligands from ethylene requires dehydrogenation, which could facilitate the formation of ethyl ligands in our system via hydrogen transfer to bound ethylene. Bound ethylidyne consists of a methyl group that is bonded to a carbon atom, which connects in a $\mu_3$-bridging fashion to a trigonal arrangement of Ir atoms, which can be located at one of the four faces of the cluster. Such a bound ethylidyne has been characterized spectroscopically on metal surfaces and structurally characterized by single-crystal X-ray diffraction of metal clusters. It has been extensively discussed as an intermediate in ethylene hydrogenation catalysis on metal surfaces.

Figure 6:
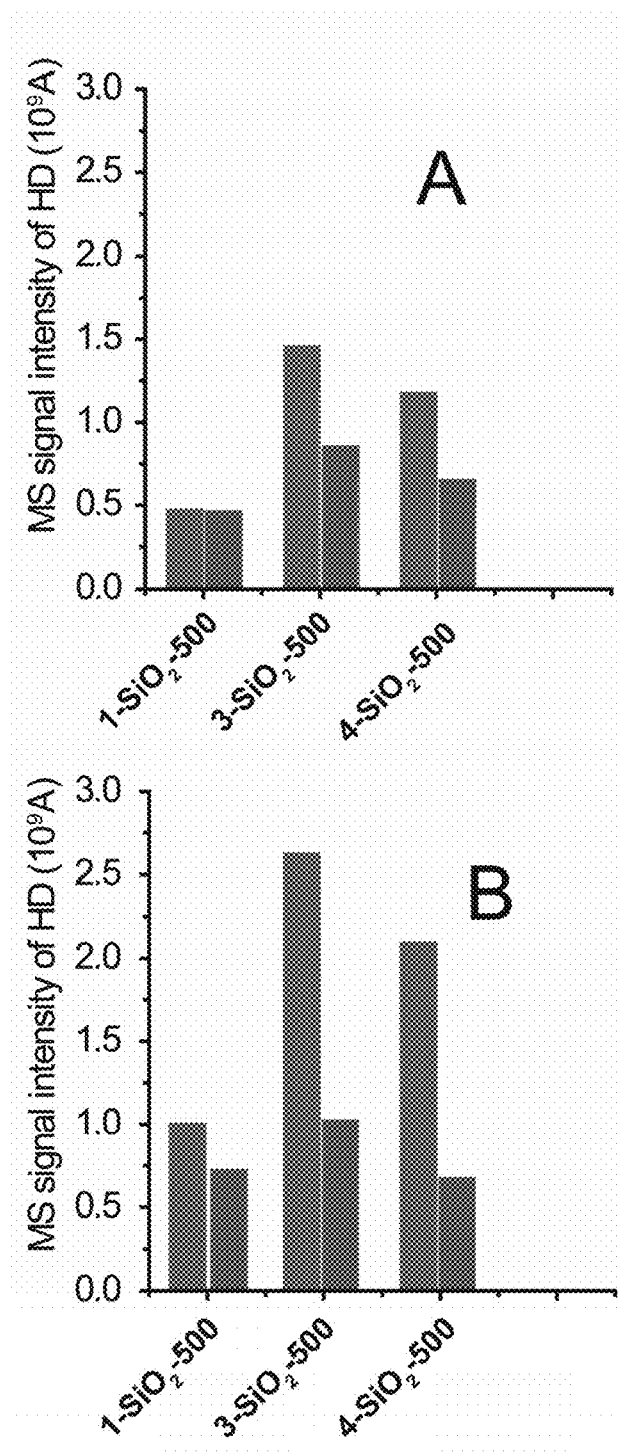
FIG. 6 shows isotopic H$_2$-D$_2$ exchange rates on various silica-supported cluster catalysts consisting of (A) as-synthesized (before ethylene hydrogenation catalysis) and (B) after 18 h of ethylene hydrogenation catalysis in a flow reactor prior to HD exchange. HD exchange conditions were 20% H$_2$, 20% D$_2$, balance: He at 40° C. for the left bars and 20% H$_2$, 20% D$_2$, 20% C$_2$H$_4$, balance: He at 40° C. for right bars. The catalyst (180 mg) was diluted with 5 g of inert, nonporous α-Al$_2$O$_3$ and was loaded into the reactor in an inert-atmosphere glove box.

Next, the consequences of these two types of sites shown in FIGS. 1a and 1b for catalysis was investigated by starting with one of the simplest possible catalytic reactions, consisting of H-D exchange in the reaction of $H_2$ with $D_2$, by flowing a gas stream over catalyst particles in a tubular packed-bed reactor and quantifying the intensity of the product HD signal intensity by mass spectrometry. The results (FIG. 6) demonstrate measurable H-D activity for all supported cluster catalysts, including closed cluster 1-$SiO_2$-500. This result confirms that hydrogen is able to bind to all the supported clusters, consistent with previous observations of the addition of hydrogen to metal clusters and H-D exchange catalysis by even closed metal carbonyl clusters. Competitive H-D exchange experiments with ethylene were carried out to further elucidate the nature of the interaction of ethylene with active sites in all of our cluster catalysts. The H-D exchange rates observed for closed 1-$SiO_2$-500 catalyst were nearly unchanged in the presence of ethylene, and remained so even after subjecting 1-$SiO_2$-500 to 18 h of continuous ethylene hydrogenation catalysis via treatment with ethylene+$H_2$ in the flow reactor. This result shows that ethylene is not a ligand that competes with hydrogen or deuterium on the closed cluster—even after significant decarbonylation occurring during ethylene hydrogenation in the gas-flow system (vide infra).

In marked contrast, open catalysts 3-$SiO_2$-500 and 4-$SiO_2$-500 showed a significant decrease in the rate of H-D exchange in the presence of ethylene versus in the absence of ethylene. This decrease corresponded to a factor of 1.7 and increased to a factor of 2.7 after the supported clusters had been subjected to 18 h of continuous ethylene hydrogenation catalysis in the flow reactor. These results show that ethylene accesses binding sites on the cluster surface when they incorporate CO vacancies formed by reactive decarbonylation using TMAO, and the ethylene on these sites restricts the bonding of hydrogen to them.

The key point is that the clusters with open sites resulting from reactive decarbonylation via TMAO treatment are uniquely accessible to ethylene, in contrast to the active sites formed by simple desorption of CO during gas flow (and during H-D exchange catalysis), whereas both kinds of sites bind and activate hydrogen. The results also support previous observations that pre-formed open ("coordinatively unsaturated") sites are not a requirement for H-D exchange catalytic activity.

Figure 7:
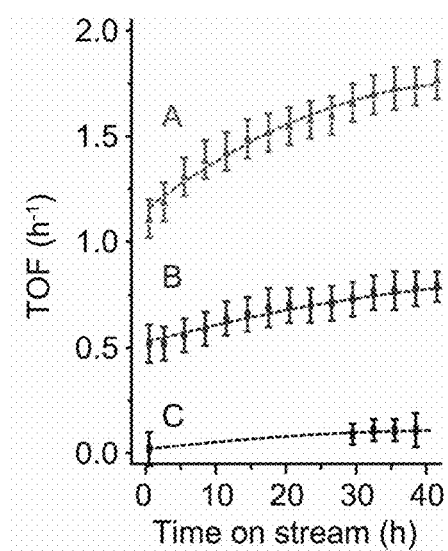
FIG. 7 shows an ethylene hydrogenation turnover frequencies for (A) 4-SiO$_2$-500, (B) 3-SiO$_2$-500, (C) 1-SiO$_2$-500. C$_2$H$_4$ hydrogenation catalysis conditions were 40° C., ambient pressure, and total flow rate of 63 mL(NTP)/min (16% H$_2$, 5% C$_2$H$_4$, balance He).

A more complex catalytic reaction was then investigated—ethylene hydrogenation—using reaction kinetics to characterize the active sites that are accessible to ethylene. Silica-supported clusters 1-$SiO_2$-500, 3-$SiO_2$-500, and 4-$SiO_2$-500 in a packed-bed U-tube gas-flow reactor were compared, and kinetics data are shown in FIG. 7. Extrapolated initial catalytic activities as well as activities after 40 h on stream are summarized in Table 2, below. The initial activity for the closed cluster catalyst 1-$SiO_2$-500 at time on stream t=0 was nearly zero (t at initial time extrapolates to TOF<0.1 $h^{-1}$). In contrast, both open clusters 3-$SiO_2$-500 and 4-$SiO_2$-500 exhibited significant activities at t=0 (initial TOF for 3-$SiO_2$-500 was 2.12 $h^{-1}$), and a 2.2-fold higher initial activity was observed for 4-$SiO_2$-500 relative to 3-$SiO_2$-500. When measured after 40 h time on stream, the catalytic activities of 3-$SiO_2$-500 and 4-$SiO_2$-500 were a factor of 7 and 16 higher, respectively, than that of 1-$SiO_2$-500. These higher catalytic activities clearly resulted from the availability of CO vacancies formed by reactive decarbonylation with TMAO. The observed reaction orders in $H_2$ and ethylene are consistent with previous reports characterizing supported $Ir_4$ and $Ir_6$ clusters as well as platinum catalysts, with the values being approximately 0.5 and zero, respectively, for both 3-$SiO_2$-500 and 4-$SiO_2$.500.

TABLE 2

Gas-phase ethylene hydrogenation TOF data for cluster catalysts 1-$SiO_2$-500, 3-$SiO_2$-500, and 4-$SiO_2$-500.

| Sample | TOF$^a$, $h^{-1}$ | |
|---|---|---|
| | 0 h time on stream | 40 h time on stream |
| 1-$SiO_2$-500 | 0.09 | 0.44 |
| 3-$SiO_2$-500 | 2.12 | 3.12 |
| 4-$SiO_2$-500 | 4.60 | 7.04 |

$^a$Catalytic activities are reported as rate of reaction per $Ir_4$ cluster (turnover frequency, TOF).

The H-D exchange rates measured for samples 1-$SiO_2$-500 and 4-$SiO_2$-500 differ by a factor of only about 2—much smaller than the difference in ethylene hydrogenation rates. Furthermore, the H-D exchange rate for 4-$SiO_2$-500 is only slightly lower than that observed for 3-$SiO_2$-500, notwithstanding the higher ethylene hydrogenation activity of the former catalyst (FIG. 7). Taken together, the data provide strong evidence that hydrogen activation is not rate limiting in ethylene hydrogenation catalysis with the supported clusters, instead pointing to ethylene binding and/or activation as being crucial.

Figure 5:
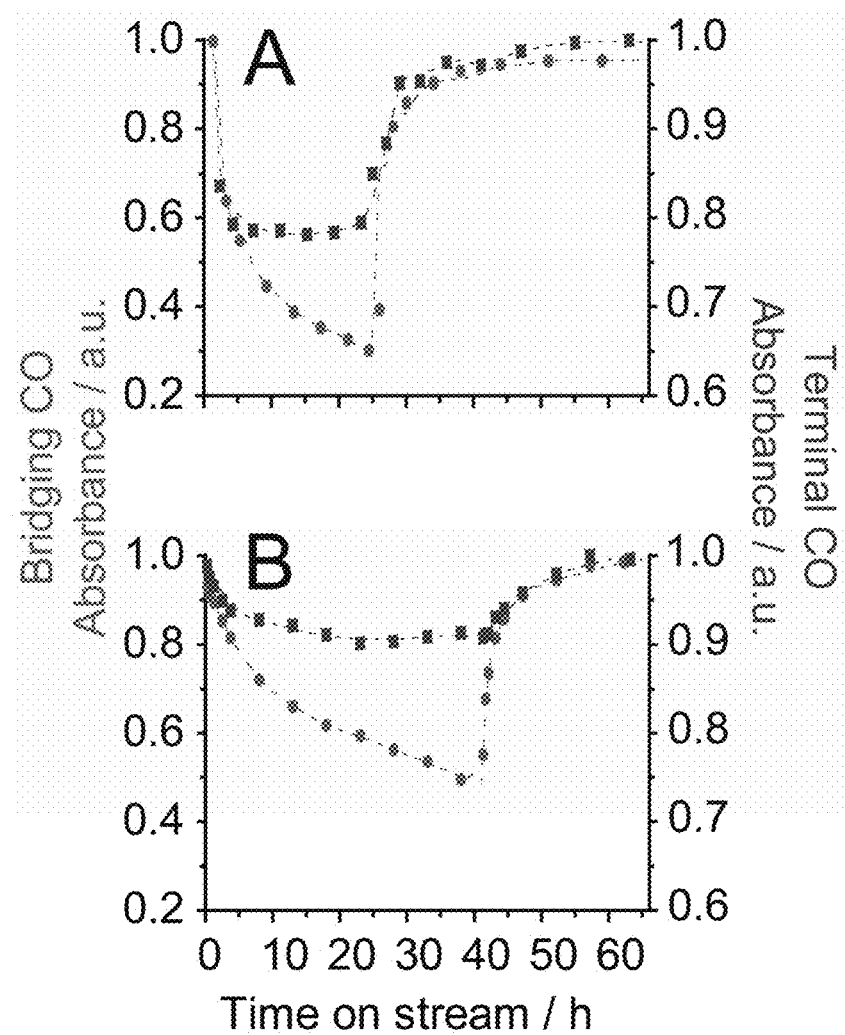
FIG. 5 shows an integrated CO intensity corresponding to bridging (circles) and terminal (squares) CO bands as measured during ethylene hydrogenation catalysis followed by recarbonylation via CO treatment, using in-situ FTIR spectroscopy of (A) 1-SiO$_2$-500 and (B) 3-SiO$_2$-500. Catalysis conditions were 40° C., ambient pressure, and total flow rate of 63 mL/min (NTP) (16% H$_2$, 5% C$_2$H$_4$, balance He) for (A) 24 h and (B) 40 h. Subsequently, a mixture of CO and He flowed at 1 and 50 mL/min (NTP), respectively, for (A) 40 h and (B) 24 h, while the IR cell temperature was held at room temperature (approximately 23° C.). Approximately 30 mg of solid powder sample in the glove box was pressed into a thin wafer and loaded into an in-situ IR flow cell equipped with CaF$_2$ windows (In-situ Research Institute, Inc., South Bend, Ind.).

With increased time on stream, the ethylene hydrogenation activities of each of the catalysts increased slightly. To understand this observation, changes in CO bands were monitored with time on stream for 1-$SiO_2$-500 and 3-$SiO_2$-500 using IR spectroscopy. Data in FIG. 5 show significant decarbonylation occurring in each catalyst during ethylene hydrogenation catalysis in the flow system. For each catalyst, the decarbonylation was found to be reversible by subsequent treatments in CO. After 25 h of ethylene hydrogenation catalyzed by 1-$SiO_2$-500, approximately 20% of the terminal and 70% of the bridging CO ligands had been removed. This extent of decarbonylation is actually greater than that observed for the open cluster 3-$SiO_2$-500, even after 40 h of ethylene hydrogenation (FIG. 5). These data imply a lack of direct correlation between catalytic activity and the number of CO vacancies synthesized on a metal cluster by decarbonylation in flowing gas. Although most CO ligands had been removed during 25 h of ethylene hydrogenation catalyzed by 1-$SiO_2$-500, the activity of this catalyst was found to be much less than that of 3-$SiO_2$-500—because in the presence of the flowing gas, CO vacancies are created that are inaccessible to ethylene and therefore inactive for ethylene hydrogenation catalysis.

Rephrased, all open ("coordinatively unsaturated") sites are equal from the perspective of CO loss and recovery; however, some vacancies are not. Those that result from reactive decarbonylation with TMAO are unique in being accessible to ethylene and activating ethylene for hydrogenation catalysis. Insofar as establishing a clear connection between ethylene binding to the metal surface as a requirement for ethylene hydrogenation catalysis, our results based on a comparison of synthetic pockets above are consistent with previous literature hypotheses, which implicate weakly π-bound ethylene as a key intermediate during hydrogenation catalysis on metals. In the preceding several decades, in microkinetic modeling of ethylene hydrogenation catalysts, S-type sites have been proposed, which selectively bind hydrogen over ethylene, as a consequence of their size differences. This size discrimination is hypothesized to be the result of carbonaceous deposits that form on the metal surface during catalysis, causing deactivation. The present observations appear to be the first experimental demonstration of the existence of such sites, whereby for the first time accessibility is controlled precisely with well-defined bound ligand arrangements on the metal surface.

The catalytic data reported here cannot be explained by cluster decomposition products, because $^{31}$P NMR data show no change in the resonances before and after catalysis, and these resonances match those observed for the corresponding clusters in solution, just prior to anchoring to silica. Thus, the phosphine ligands remained intact and within the same local environment during anchoring and catalysis. HAADF-STEM data also show a lack of change in the metal cluster framework size, when comparing samples before and after catalysis as well as before and after anchoring to silica. Even when the metal clusters were intentionally aggregated (by use of forcing conditions of catalysis higher temperature), the catalytic activity did not change significantly (the same activation energy as at lower temperatures was observed). These data disqualify metal aggregation as an explanation for the observed catalytic activity increases.

The remarkable feature of open sites created by simple dissociation of CO versus reactive decarbonylation with TMAO is that the former treatment led to synthesis of sites that have unprecedented ability to discriminate between ethylene and CO/hydrogen, whereas the latter are accessible to all three. The subtle structural control required to discriminate between these molecules of nearly equal size demonstrates the presence of size-selective molecular pockets at the interface between the metal cluster and the ligands bound to it. Furthermore, the results demonstrate a complete lack of scrambling of CO vacancies between configurations in FIGS. 1a (corresponding to decarbonylation by simple dissociation) and 1b (corresponding to reactive decarbonylation with TMAO). Related scrambling processes have been observed in decarbonylated iridium clusters. The results instead indicate that the open structure of the site in FIG. 1b is synthesized so as to be accessible to ethylene—and this accessibility results from the use of a bulky oxidant—a result unprecedented in cluster chemistry.

In summary, the results shown here demonstrate two new phenomena, which are envisioned to have broad applicability in fundamental catalysis science and potentially even in technology dealing with catalysis and gas purification: (i) the ability of one set of synthetic pockets to completely shun ethylene while providing ready access to hydrogen and CO for binding; and (ii) the ability to synthetically tune pockets so as to allow access of ethylene, CO, and hydrogen and facilitate catalysis involving ethylene. The synthesis of selective molecular pockets, which provide a controllable degree of access to vacancies on the underlying metal surface for binding and activating substrates, has potentially profound and broad repercussions for control of catalysis and separations of gas mixtures. A selective adsorbent for gas mixture or a selective catalyst can be prepared, for example, by a fluid-flow treatment of a CO-ligand containing metal surface at an appropriate, chosen temperature so as to cause decarbonylation.

Figure 9:
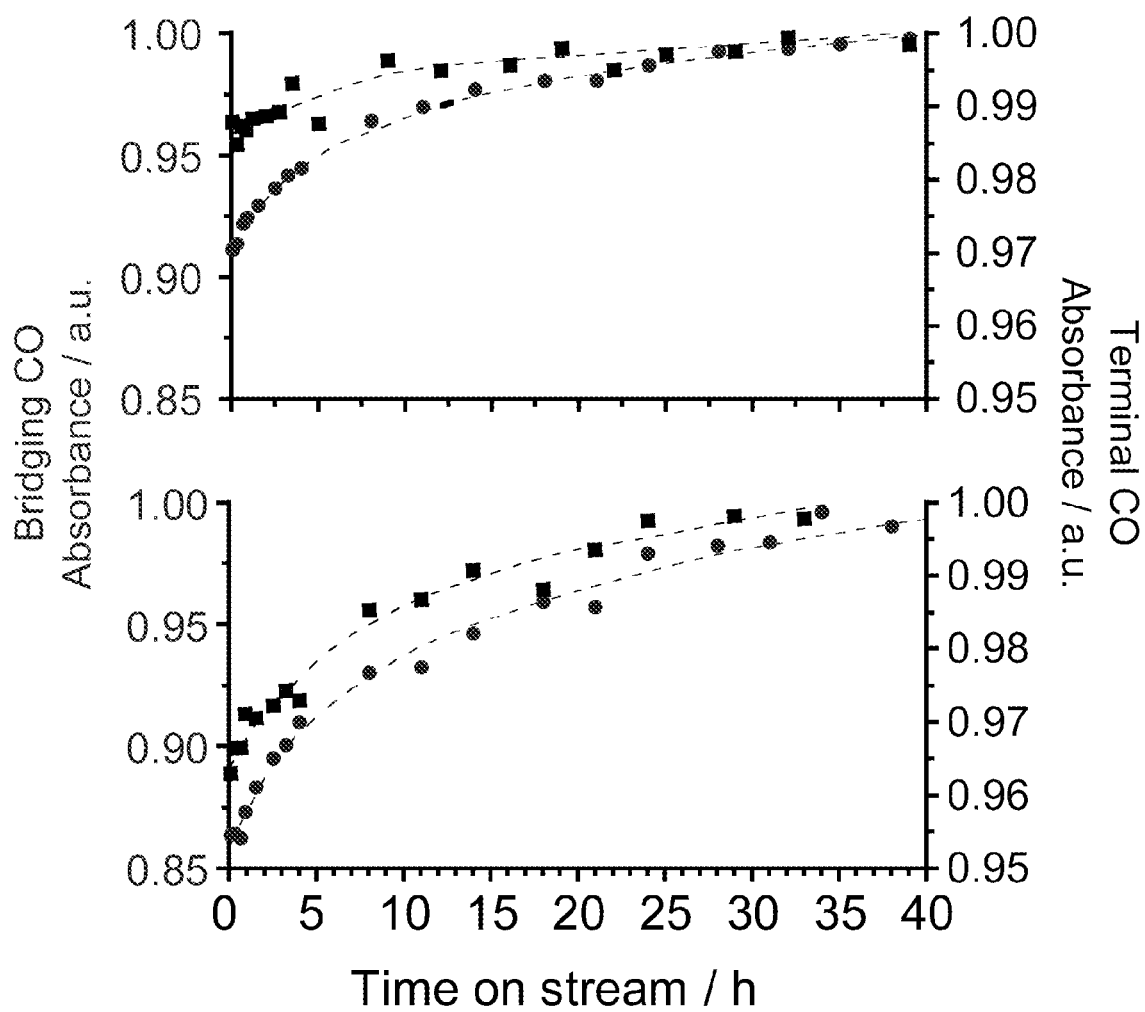
FIG. 9 shows CO absorbance intensity corresponding to bridging (circles) and terminal (squares) CO bands as measured during recarbonylation of 3-SiO$_2$-500 (top) and 4-SiO$_2$-500 (bottom) using in-situ solid-state IR spectroscopy. During the experiment, a mixture of CO and He flowed at 1 and 50 mL(NTP)/min, respectively, for (top) 40 h and (bottom) 24 h, while the IR cell temperature was held at room temperature (approximately 23° C.). A value of 1.0 was arbitrarily assigned to the absorbance intensity (measured at the maximum) after 40 h of CO treatment.

Further Experiments:

Recarbonylation of the supported open clusters 3-SiO$_2$-500 and 4-SiO$_2$-500 was investigated. The data are summarized in Table 3 below. Both of these supported clusters were recarbonylated to an extent corresponding to approximately 50% of that observed for the unsupported clusters in decane solution. The difference cannot be ascribed to remaining trimethylamine because it was removed during evacuation of supported catalysts (vide supra). IR data (see FIG. 9) show that treatment of 3-SiO$_2$-500 and 4-SiO$_2$-500 with CO resulted in gradual recarbonylation over 40 h. This observation is in contrast to the complete recarbonylation in 2 h of the corresponding open clusters in decane solution. The slowing of the recarbonylation and the decrease in recarbonylation capacity observed for the supported clusters cannot be ascribed to mass transport restrictions, because recarbonylation of supported clusters (such as shown in FIG. 3a) can intrinsically occur much faster. Instead, we attribute the observations to the influence of the silica support acting as a competitive ligand—blocking open sites from recarbonylation, even though silica is a support that is expected to minimize such interactions. Similar support effects may account for previous observations of partial recarbonylation—recarbonylation of fully decarbonylated Ir$_4$ clusters supported on partially dehydroxylated MgO led to only 13% of the open sites being recarbonylated. The results summarized above demonstrate that CO can access open sites on the supported clusters.

TABLE 3

Characterization of supported cluster samples 3-SiO$_2$-500 and 4-SiO$_2$-500 using IR carbonyl-band absorbance intensities[b] after recarbonylation

| Sample | # (CO) gained[a] | CO$_{term}$/% | CO$_{bridg}$/% |
|---|---|---|---|
| 3-SiO$_2$-500 (recarb) | 0.3 | 93 | 80 |
| 4-SiO$_2$-500 (recarb) | 0.5 | 90 | 63 |

[a]# = number of CO molecules per Ir$_4$ cluster
[b]Absorbance intensities were measured at 1994 cm$^{-1}$ for terminal CO ligands and at 1784 cm$^{-1}$ for bridging CO ligands after subtraction of the Si—O—Si peak at 1868 cm$^{-1}$. The reported relative intensities (as a %) are normalized to the absorbance intensity of 1, by assuming that the state of clusters 3 and 4 supported on silica is identical to that reported in Table 1 in decane solution.

Decarbonylation and Recarbonylation of Cluster 1 Using 1 Equivalent of Me$_3$NO in Solution To a solution of 51 mg (0.013 mmol) cluster 1 in 3 mL decane was added 100 μL of a solution of 100 mg (1.33 mmol) Me$_3$NO in 10 mL dichloromethane. The solution color changed immediately from yellow to brown. After 1 h, the head space of the schlenk flask was evacuated and purged with CO gas. The color of the solution immediately changed from brown to yellow. Samples for DLS, NMR and FTIR spectroscopy were taken before Me$_3$NO addition, after Me$_3$NO addition, and after CO treatment. In addition to DLS data mentioned in the manuscript, which shows lack of cluster aggregation for 3 and 4, we monitored the reactive decarbonylation process using TMAO via $^1$H NMR spectroscopy with the sample in $C_6D_{12}$ solution. Although the $^1$H NMR spectra of 3 and 4 did not change during decarbonylation, which is yet another indication of retention of cluster stability, a new resonance appeared at 2.14 ppm, which is assigned to bound $Me_3N$ (we measured the chemical shift of $Me_3N$ via $^1$H NMR in the same solvent as the experiment at 2.12 ppm, which is consistent with the previously assigned $^1$H NMR $Me_3N$ resonance. Such a small shift of bound versus free $Me_3N$ is expected on the basis of previous measurements of trimethylamine coordinated to neutral tetrahedral metal carbonyl clusters. $Me_3N$ was removed (verified by absence of resonance in the $^1$H NMR spectrum) by evacuating 3 (for 15 h) and 4 (for 0.5 h) at 10 Pa at room temperature after synthesis. This result means that the final state of anchored clusters 3 and 4 on a silica support consists of CO vacancies, rather than bound $Me_3N$, since these clusters were similarly evacuated after anchoring.

Decarbonylation and Recarbonylation of Cluster 1 Using 2 Equivalents of $Me_3NO$ in Solution To a solution of 51 mg (0.013 mmol) cluster 1 in 3 mL decane was added 195 μL of a solution of 100 mg (1.33 mmol) $Me_3NO$ in 10 mL dichloromethane. The solution color changed immediately from yellow to brown. After 1 h, the head space of the Schlenk flask was evacuated and purged with CO gas. The color of the solution immediately changed from brown to yellow. Samples for DLS, NMR and FTIR spectroscopy were taken before $Me_3NO$ addition, after $Me_3NO$ addition, and after CO treatment.

Decarbonylation and Recarbonylation of Cluster 2 Using 1 Equivalent of $Me_3NO$ in Solution To a solution of 12 mg (0.007 mmol) cluster 1 in 2 mL decane was added 55 μL of a solution of 100 mg (1.33 mmol) $Me_3NO$ in 10 mL dichloromethane. The solution color changed immediately from yellow to brown and the formation of a brown solid was observed. After 1 h, the head space of the Schlenk flask was evacuated and purged with CO gas. Samples for DLS, NMR and FTIR spectroscopy were taken before $Me_3NO$ addition, after $Me_3NO$ addition, and after CO treatment.

The Following Procedures were Used in the Foregoing Experimental Runs:

Analysis of Liquid Samples

Infrared spectroscopy in solution was performed on a Bruker Tensor instrument using a liquid cell ($CaF_2$ windows, d=0.5 mm). $^1$H and $^{31}$P $\{^1H\}$-NMR spectra in solution were recorded in either decane-$d_{12}$ or cyclohexane-$d_{12}$ (293 K), using either a Bruker AV-600 (600 MHz) instrument, an AVQ-400 (400 MHz), or an AVB-400 (400 Mhz) instrument at the UC Berkeley College of Chemistry NMR Facility. $^{31}$P NMR data were referenced relative to trimethyl phosphate. $^1$H-NMR data were referenced to Tetramethylsilane (δ=0 ppm). DLS was performed on a Malvern Nano-Zetasizer in glass cuvettes at 25° C. Solvents were filtered through 0.02 μm filters prior use. Samples were given sufficient time to equilibrate to 25° C. The results from at least four measurements are averaged and the number-average particle size values are reported.

Catalysis

Catalytic $C_2H_4$ hydrogenation reactions were carried out in once-through packed-bed flow reactors at a temperature of 40° C. and atmospheric pressure. The packed bed (250 mg of catalyst) was loaded into a u-shaped reactor (with air-free stopcock closures) in an argon-filled glovebox, and installed into the flow system to avoid contacting the catalyst with air. The process lines, and subsequently the catalyst packed bed, were purged with He (Praxair, 99.999%). The temperature of the packed bed was measured by using a thermocouple placed inside the reactor and immediately upstream of the packed bed. The reactant gases (10 mL(NTP)/min $H_2$ (Praxair, 99.999%) and 3 mL(NTP)/min $C_2H_4$ (Praxair, 99.999%)) were diluted in a stream of He (99.999%) flowing at 50 mL(NTP)/min. These gases were further purified by passage through traps to remove traces of $O_2$, moisture, and hydrocarbons prior to contact with the catalyst. An online MKS FTIR (Multigas 2030) was used to analyze the reaction products.

Solid State FTIR

A Nicolet 6700 FTIR spectrometer with a spectral resolution of 4 $cm^{-1}$ was used to collect transmission IR spectra. Approximately 30 mg of solid powder sample in the glove box was pressed into a thin wafer and loaded into an in-situ IR flow cell equipped with $CaF_2$ windows (In-situ Research Institute, Inc., South Bend, Ind.). The cell is connected to a flow system controlled by mass flow controllers. The sample wafer can be heated and its temperature is monitored by a K-type thermocouple. Each spectrum represents the average of 32 scans.

$H_2/D_2$ Exchange

Measurements of mass spectra were carried out to determine the products of the reaction in a once-through steady-state tubular plug-flow reactors at 313 K and 1 bar. The catalyst (180 mg) was diluted with 5 g of inert, nonporous α-$Al_2O_3$ and was loaded into the reactor in an inert-atmosphere glove box. The feed consisted of $C_2H_4$, $H_2$, and $D_2$ (the partial pressure of each was 200 mbar balanced in helium) with the total flow rate being 100 mL(NTP)/min and the total pressure being atmospheric. The temperature was 313±1 K. The concentration of HD in the effluent stream was measured with a mass spectrometer. Silica support alone is not active for the H-D exchange reaction. Mass spectra of the gases introduced into the flow system and the effluents produced by reaction were measured with an online Balzers OmniStar mass spectrometer running in multi-ion monitoring mode. Specifically, changes in the signal intensities of $H_2$ (m/z=2), $D_2$ (m/z=4), HD (m/z=3), CO (m/z=28), $C_2H_4$ (m/z=26, 27, and 28), $C_2H_6$ (m/z=26, 27, 28, and 30), $C_4H_8$ (m/z=41 and 55), and $C_4H_{10}$ (m/z=43 and 56) were recorded. The reported intensity values were corrected by subtracting background intensities recorded while the reaction gas mixture was bypassing the flow reactor containing the catalyst. The error bound, correspond to the standard deviation of the measurements, is estimated to be ±1%.

TEM

In the STEM experiments, to minimize the exposure to air and moisture, powder samples were loaded onto a lacey carbon, 300-mesh copper grid (Ted-Pella) in the glovebox. The grid in the glovebox was packed in an Eppendorf tube and sealed with Parafilm. Each Eppendorf tube was placed in a Swagelok stainless-steel tube sealed with O-rings for transfer to the microscope. There, an argon-filled glovebag (Glas-Col) was purged five times with ultrahigh purity argon, and the TEM grid was loaded onto the TEM holder in the glovebag under a blanket of flowing argon. As argon flowed over the TEM holder, it was transferred from the glovebag to the microscope with an air exposure of at most 4 s.

Images were obtained with a JEOL JEM-2100F electron microscope equipped with an FEG, operated at 200 kV, with a CEOS hexapole probe (STEM) aberration corrector. The images were captured by a HAADF detector with a collection semi-angle of 75-200 mrad and a probe convergence semi-angle of 17.1 mrad. The imaging dose was approximately 105 e-Å-2. Prior to imaging of the samples, the aberration corrector was aligned with a Pt/Ir on holey carbon standard sample (SPI supplies) until atomic resolution of the metals was achieved and the lattice spacings of the metals were confirmed. Images were obtained in <5 s including instrument optimization prior to image acquisition, minimizing the occurrence of electron beam damage.

A total of approximately 30 clusters were analyzed for size measurement for each set of samples. The average cluster diameter is reported with a standard deviation for the population of clusters analyzed. For each cluster, an intensity profile was obtained by using the Digital Micrograph software (Gatan). Line profiles were then transferred to OriginPro for baseline correction. Background-subtracted profiles of the clusters were fitted to a Gaussian distribution function in OriginPro, and FWHM values of the fitted peak are reported as the diameter of each cluster metal framework. Accordingly, the mean diameter and the standard deviation for the sample are reported.

All patents and publications referenced herein are hereby incorporated by reference, in their entirety, to the extent not inconsistent with the present disclosure. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. An organic ligand-bound metal surface, which is on a solid support, having one or more vacant binding sites that selects one fluid species over another, which sites have been created by flowing of inert gas over the metal surface for CO dissociation.

2. The ligand-bound metal surface of claim 1, wherein the selection of fluid species is between two closely sized molecular species having less than 5 Angstrom difference in kinetic diameter.

3. The ligand-bound metal surface of claim 1, wherein the selection of fluid species is between two closely sized molecular species having less than 3 Angstrom difference in kinetic diameter.

4. The ligand-bound metal surface of claim 1, wherein the selection of fluid species is between two closely sized molecular species having less than 2 Angstrom difference in kinetic diameter.

5. The ligand-bound metal surface of claim 1, wherein the selection of fluid species is between two closely sized molecular species having less than 1 Angstrom difference in kinetic diameter.

6. The ligand-bound metal surface of claim 5, wherein the two molecular species include carbon monoxide and ethylene.

7. The ligand-bound metal surface of claim 1, wherein the metal is a metal cluster with a tetrahedral framework.

8. The ligand-bound metal surface of claim 7, wherein the metal is a metal cluster or a metal nanoparticle.

9. The ligand-bound metal surface of claim 8, wherein the metal is a metal cluster.

10. The ligand-bound metal surface of claim 9, wherein the metal cluster comprises an $Ir_4$ or $Ir_6$ cluster.

11. The ligand-bound metal surface of claim 9, wherein the metal cluster comprises a $Rh_4$ or $Rh_6$ cluster.

12. The ligand-bound metal surface of claim 1, wherein the ligand is an electron donating ligand.

13. The ligand-bound metal surface of claim 12, wherein the ligand incorporates a phosphine group.

14. The ligand-bound metal surface of claim 12, wherein the ligand incorporates a calixarene.

15. A ligand-bound metal surface, which is on a solid support, having one or more vacant binding sites that selects one fluid species over another.

16. The ligand-bound metal surface of claim 15, wherein the selection of fluid species is between two closely sized molecular species having less than 5 Angstrom difference in kinetic diameter.

17. The ligand-bound metal surface of claim 15, wherein the selection of fluid species is between two closely sized molecular species having less than 3 Angstrom difference in kinetic diameter.

18. The ligand-bound metal surface of claim 15, wherein the selection of fluid species is between two closely sized molecular species having less than 1 Angstrom difference in kinetic diameter.

19. The ligand-bound metal surface of claim 15, wherein the selection of fluid species is between two closely sized molecular species having less than 1 Angstrom difference in kinetic diameter.

20. The ligand-bound metal surface of claim 19, wherein the two molecular species include carbon monoxide and ethylene.

21. The ligand-bound metal surface of claim 15, wherein the metal is that of a metal cluster with a tetrahedral framework.

22. The ligand-bound metal surface of claim 21, wherein the metal cluster comprises an $Ir_4$ or $Ir_6$ cluster.

23. The ligand-bound metal cluster of claim 21, wherein the metal cluster comprises a $Rh_4$ or $Rh_6$ cluster.

24. The ligand-bound metal cluster of claim 21, wherein the ligand is an electron donating ligand.

25. The ligand-bound metal cluster of claim 24, wherein the ligand incorporates a phosphine group.

26. The ligand-bound metal cluster of claim 24, wherein the ligand incorporates a calixarene.

27. The ligand-bound metal cluster of claim 21, wherein the radius of curvature of at least one of the ligands is greater than that of the metal cluster.

28. A method of separating one or more fluid species from others, comprising passing a mixture of fluid species over the ligand-bound metal surface of claim 1, and recovering a fluid stream comprising the fluid species not bound to the ligand-bound metal surface.

29. The method of claim 28, wherein the mixture comprises carbon monoxide and ethylene.

30. The method of claim 28, wherein the ligand-bound metal surface is on either a metal, metal-oxide, or ceramic support.

31. A sensor for carbon monoxide, which comprises the ligand-bound metal surface of claim 1.

32. A catalyst comprised of the ligand-bound metal surface of claim 1.

33. The ligand-bound metal surface of claim 1, wherein the metal surface is on a silica support.

34. The method of claim 30, wherein the support is a silica support.

* * * * *

UNITED STATES PATENT AND TRADEMARK OFFICE
CERTIFICATE OF CORRECTION

PATENT NO. : 9,575,042 B2
APPLICATION NO. : 14/292252
DATED : February 21, 2017
INVENTOR(S) : Alexander Okrut et al.

It is certified that error appears in the above-identified patent and that said Letters Patent is hereby corrected as shown below:

In the Specification

In Column 1, Lines 12-13, replace "contract number DE-SC0005822 awarded by the Department of Energy." with --contract number DE-FG02-04ER15513 awarded by the Department of Energy.--

Signed and Sealed this
Twenty-eighth Day of May, 2024

Katherine Kelly Vidal
Director of the United States Patent and Trademark Office